United States Patent [19]

Hammons et al.

[11] Patent Number: 5,647,863

[45] Date of Patent: Jul. 15, 1997

[54] ABSORBENT ARTICLE WITH CLEAN APPEARANCE AND CAPACITY SIGNAL MEANS

[75] Inventors: John L. Hammons, Hamilton; Shannon J. Hennessy; Alvin D. Martin, Jr., both of Cincinnati, all of Ohio

[73] Assignee: The Procter & Gamble Company, Cincinnati, Ohio

[21] Appl. No.: 531,533

[22] Filed: Sep. 21, 1995

[51] Int. Cl.$^6$ .............................. A61F 13/15; A61F 13/20

[52] U.S. Cl. .................... 604/378; 604/361; 604/366; 604/367; 604/385.1

[58] Field of Search ...................... 604/358, 361, 604/362, 365–366, 367, 368, 372, 378–380, 385.1, 386

[56] References Cited

U.S. PATENT DOCUMENTS

| | | |
|---|---|---|
| 4,029,101 | 6/1977 | Chesky et al. . |
| 4,184,498 | 1/1980 | Franco . |
| 4,212,302 | 7/1980 | Karami ........................... 604/368 |
| 4,342,314 | 8/1982 | Radel et al. . |
| 4,629,643 | 12/1986 | Curro et al. . |
| 4,834,735 | 5/1989 | Alemany et al. . |
| 4,973,325 | 11/1990 | Sherrod et al. . |
| 5,151,091 | 9/1992 | Giaug et al. . |
| 5,219,341 | 6/1993 | Serbiak et al. . |
| 5,248,309 | 9/1993 | Serbiak et al. . |
| 5,271,987 | 12/1993 | Iskra . |
| 5,294,478 | 3/1994 | Wanek et al. . |
| 5,342,336 | 8/1994 | Meirowitz et al. . |
| 5,352,217 | 10/1994 | Curro . |
| 5,364,382 | 11/1994 | Latimer et al. . |
| 5,374,260 | 12/1994 | Lemay et al. . |
| 5,382,245 | 1/1995 | Thompson et al. . |
| 5,401,267 | 3/1995 | Couthre-Dorschner et al. . |
| 5,415,640 | 5/1995 | Kirby et al. . |
| 5,429,629 | 7/1995 | Latimer . |
| 5,454,800 | 10/1995 | Hirt et al. . |
| 5,525,407 | 6/1996 | Yang . |

FOREIGN PATENT DOCUMENTS

| | | |
|---|---|---|
| 0472633B1 | 2/1993 | European Pat. Off. . |
| 0572033A2 | 12/1993 | European Pat. Off. . |
| 0666350A1 | 8/1995 | European Pat. Off. . |
| 0670154A2 | 9/1995 | European Pat. Off. . |
| 0687453A1 | 12/1995 | European Pat. Off. . |
| 0685212A2 | 12/1995 | European Pat. Off. . |
| 2165757 | 4/1986 | United Kingdom . |
| 9119471 | 12/1991 | WIPO ................................ 604/361 |
| WO93/21881 | 11/1993 | WIPO . |
| WO94/16658 | 8/1994 | WIPO . |
| WO94/26221 | 11/1994 | WIPO . |
| WO95/01146 | 1/1995 | WIPO . |
| WO95/10996 | 4/1995 | WIPO . |
| WO95/17149 | 6/1995 | WIPO . |
| WO95/17150 | 6/1995 | WIPO . |

*Primary Examiner*—P. Zuttarelli
*Attorney, Agent, or Firm*—Edward J. Milbrada; Steven W. Miller; Jeffrey V. Bamber

[57] ABSTRACT

An absorbent article, such as a sanitary napkin, comprising a topsheet, a backsheet, and an absorbent core is described. The absorbent core comprises an acquisition member, a storage/distribution member, and an indicator member. The absorbent article further has a longitudinally oriented middle region defined by the storage/distribution member and a pair of longitudinally oriented side regions that lie laterally outboard of the middle region. The acquisition member is disposed on the storage/distribution member and the indicator member is disposed, at least partially, in the side regions. The storage/distribution member has a higher capillary suction than the acquisition member such that absorbed bodily fluids are drawn from the acquisition member into the storage/distribution member providing a clean appearance. The capillary suction of the storage/distribution member is also higher than the capillary suction of the indicator member so that the indicator member is not noticeably stained until the absorbent capacity of the storage/distribution member is substantially exhausted thus providing a signal that it is time to change when such staining becomes apparent.

20 Claims, 6 Drawing Sheets

ABSORBENT ARTICLE WITH CLEAN APPEARANCE AND CAPACITY SIGNAL MEANS

FIELD OF THE INVENTION

The present invention relates to absorbent articles, particularly sanitary napkins. More particularly, the present invention relates to sanitary napkins which store the bulk of absorbed bodily fluids in the middle portion thereof and which provide a means for signaling when the absorbent capacity of the sanitary napkin is being approached.

BACKGROUND OF THE INVENTION

Absorbent articles, such as sanitary napkins, panty liners, and incontinence pads that are designed to absorb and retain liquids and other discharges from the human body and to prevent body and clothing soiling, having various different constructions are well known.

The current tendency has been to develop absorbent articles such as sanitary napkins which are increasingly thinner and conform better to the body. Recently, efforts have been directed to developing thinner sanitary napkins which have the capacity to absorb and contain medium to high menstrual discharges. Previously, such discharges could only be handled by relatively thick sanitary napkins. Examples of thin sanitary napkins having capacities great enough to handle medium to high menstrual flows are disclosed in U.S. Pat. Nos. 4,950,264 and 5,009,653, issued to Osborn, on Aug. 21, 1990 and Apr. 23, 1991, respectively.

One of the main objectives in developing absorbent articles is to utilize the entire capacity of the absorbent article. The utilization of the capacity for absorption of menses and other bodily exudates in the thin sanitary napkins described in the Osborn references is achieved at least in part by the presence of a "wipe acquisition sheet" that distributes the exudates more evenly over the underlying absorbent core. In general, products that are not provided with a structure like the wipe acquisition sheet described in the aforementioned patents, typically distribute liquids in a circular pattern, resulting in liquids reaching the longitudinal side edges of the absorbent article before the end regions of the absorbent article are utilized. When liquids come near the longitudinal side edges of the absorbent article, the chance for leakage from the sides of the product increases, despite available absorbent capacity in the end regions of the absorbent article. Even if the absorbent capacity of the end region is more fully utilized, a signal that the absorbent capacity of the absorbent article is being approached is desirable to users in order that the user may change the article before leakage and resultant staining can occur. Further, users have shown a preference for absorbent articles having a clean and dry appearance, even after much of the absorbent capacity of the absorbent article has been used.

In the past, a number of efforts have been made to direct exudates in an attempt to utilize more of the absorbent capacity of an absorbent article. A number of these efforts have used absorbent means or densification of absorbent means. Some of such efforts are described in U.S. Pat. No. 4,678,453 issued Jul. 7, 1987 to Holtman and U.S. Pat. No. 4,624,666 issued Nov. 25, 1986 to DeRossett, et al. Absorbent articles which use absorbent means to direct fluid flow, however, are typically subject to the disadvantage that the absorbent means will tend to become saturated and interfere with its fluid directing capabilities.

Another series of patents teaches the use of baffles, barriers, and transfer members for liquid transport. For instance, U.S. Pat. No. 4,029,101 issued Jun. 14, 1977 to Chesky et al. discloses using an elongated baffle near the base of the pad. U.S. Pat. No. 3,736,931 issued Jun. 5, 1973 to Glassman discloses using a moisture impervious layer in the pad. However, in both of these examples, liquids may wick laterally before reaching the baffle or the moisture impervious layer. This may tend to cause side failure (or side leakage), particularly when the pad bunches during wear. In such cases, the barrier or transfer member may be disturbed by the bunching of the pad, and body fluids may circumvent the barder or transfer member and flow directly toward the longitudinal side edges of the product.

Attempts have also been made to provide a signal that it is time to change the article. For example, U.S. Pat. No. 5,401,267 issued to Couture-Dorschner on Mar. 28, 1995 describes an absorbent article having first and third members with a high wicking capacity and a second member with a lower wicking capacity. The second member has a width equal to or greater than either of the first or third members and is said to provide a visual signal that it is time to change the article when it appears to be soiled. However, the first member thereof lies immediately below the cover sheet so the body contacting surface of such an absorbent article may appear to be soiled, even with unused absorbent capacity.

Thus, a need exists for an absorbent article, such as a sanitary napkin that has an improved means for drawing bodily exudates from the surface thereof and distributing the exudates so that the exudates will not reach the longitudinal side edges of the absorbent article before the absorbent capacity of the absorbent article is substantially exhausted, thus maintaining a relatively clean appearance for the majority of the wear cycle of the absorbent article.

It is, therefore, an object of the present invention to provide an absorbent article, such as a sanitary napkin, with a means for drawing fluid from the surface to the middle of the absorbent article and for insuring the absorbent capacity of the sanitary napkin is substantially exhausted before liquids reach the longitudinal side edges of the napkin.

It is another object of the present invention to provide a signal to a user that the absorbent capacity of the absorbent article is substantially exhausted and that it is time to change.

SUMMARY OF THE INVENTION

The present invention is directed to an absorbent article, such as a sanitary napkin. More preferably, the present invention is directed to a sanitary napkin with a means for maintaining a relatively clean appearance for the majority of the wear cycle and for signaling to a wearer that the absorbent capacity of the sanitary napkin is being approached.

The sanitary napkin of the present invention has a longitudinal centerline, a transverse centerline, a body-facing surface, and a garment-facing surface. The sanitary napkin comprises a liquid pervious topsheet, a liquid impervious backsheet joined to the topsheet, and an absorbent core positioned between the topsheet and backsheet. In a preferred embodiment of the present invention, the absorbent core comprises an acquisition member, a storage/distribution member, and an indicator member. These elements comprising the absorbent core co-operate such that the bulk of the absorbent capacity of the sanitary napkin is provided by the storage/distribution member positioned in a middle portion of the sanitary napkin which, because of relative capillarities, draws fluids away from other members and distributes them within its volume so that the bulk of the absorbed fluid is stored in the middle of the sanitary napkin away from the body surface and edges thereof. When the absorbent capacity of the storage/distribution member is substantially exhausted, the indicator member begins to become soiled and signals a user that it is time to change sanitary napkins.

BRIEF DESCRIPTION OF THE DRAWINGS

While the specification concludes with claims particularly pointing out and distinctly claiming the subject matter which is regarded as forming the present invention, it is believed that the invention will be better understood from the following description taken in conjunction with the accompanying drawings, in which:

DETAILED DESCRIPTION OF PREFERRED EMBODIMENTS

1. General Characteristics of the Absorbent Article.

Figure 1:
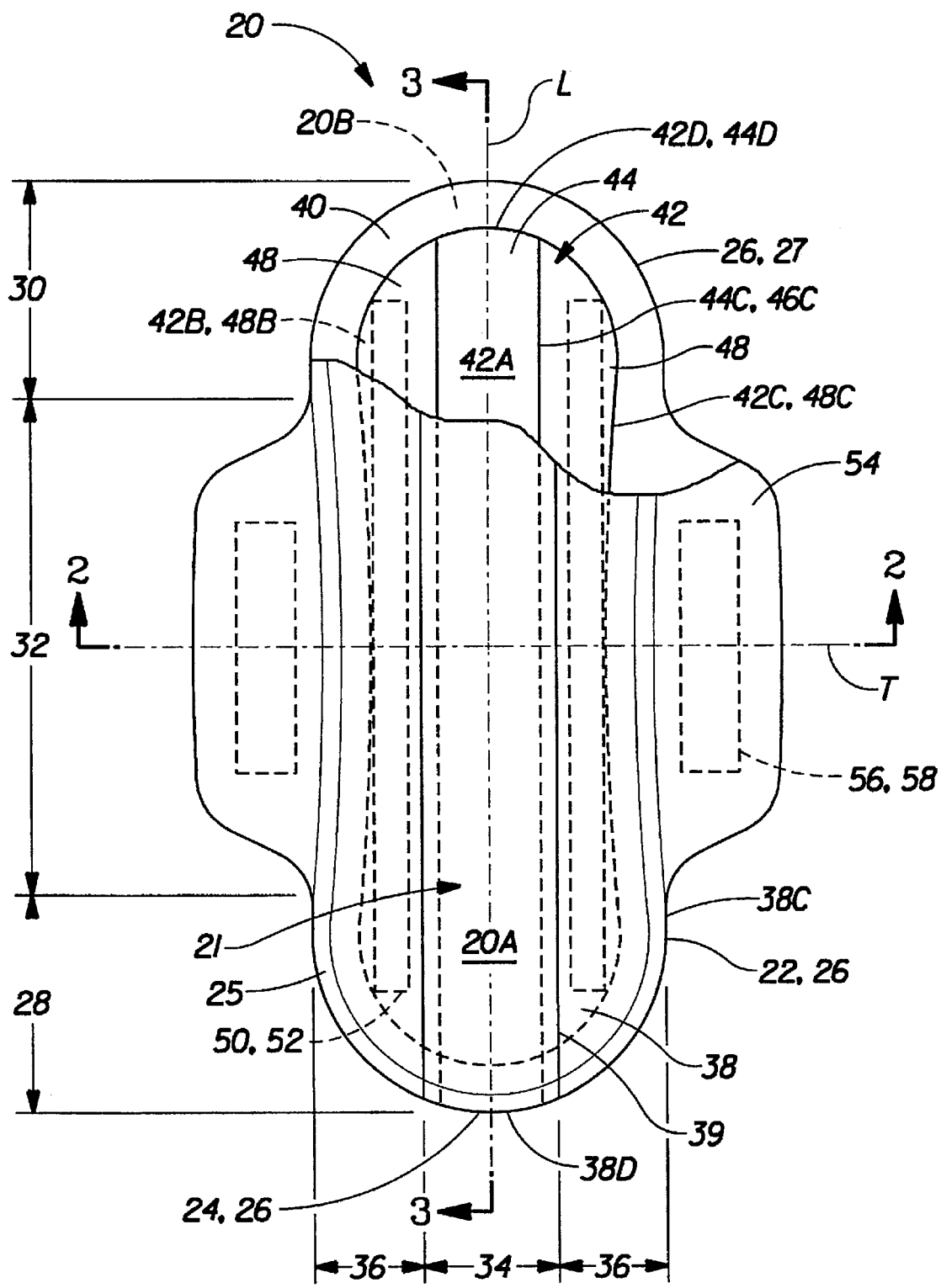
FIG. 1 is a top plan view of a preferred sanitary napkin embodiment of the present invention shown with a portion of the topsheet removed to show the underlying structure.

FIG. 1 shows a particularly preferred embodiment of the disposable absorbent article of the present invention, sanitary napkin 20.

The term "absorbent article", as used herein, refers to devices which absorb and contain body exudates, and, more specifically, refers to devices which are placed against or in proximity to the body of the wearer to absorb and contain the various exudates discharged from the body. The term "disposable" is used herein to describe absorbent articles which are not intended to be laundered or otherwise restored or reused as an absorbent article (i.e., they are intended to be discarded after a single use, and, preferably, to be recycled, composted or otherwise disposed of in an environmentally compatible manner).

The term "sanitary napkin", as used herein, refers to an absorbent article which is worn by females adjacent to the pudendal region, generally external to the urogenital region, and which is intended to absorb and contain bodily fluids such as blood, menses, and urine. As used herein, the terms "fluid", "liquid" and the like are intended to be interchangeable and refer to materials that are in a liquid state when they are at a temperature of about 100° F. It should be understood, however, that the present invention is also applicable to other feminine hygiene or catamenial pads such as panty liners, or other absorbent articles such as incontinence pads, and the like.

The sanitary napkin 20 has two surfaces, a body-contacting surface or "body surface" 20A and a garment surface 20B. The sanitary napkin 20 is shown in FIG. 1 as viewed from its body surface 20A. The body surface 20A is intended to be worn adjacent to the body of the wearer while the garment surface 20B is on the opposite side and is intended to be placed adjacent to the wearer's undergarments when the sanitary napkin 20 is worn.

The sanitary napkin 20 has two centerlines, a longitudinal centerline L and a transverse centerline T. The term "longitudinal", as used herein, refers to a line, axis or direction in the plane of the sanitary napkin 20 that is generally aligned with (i.e., approximately parallel to) a vertical plane which bisects a standing wearer into left and right body halves when the sanitary napkin 20 is worn. The terms "transverse" or "lateral" as used herein, are interchangeable, and refer to a line, axis or direction which lies within the plane of the sanitary napkin 20 that is generally perpendicular to the longitudinal direction. The sanitary napkin 20 has a longitudinal dimension or length that runs in the general direction of the longitudinal centerline L, and a (typically shorter) transverse dimension or width that runs in the general direction of the transverse centerline T.

The sanitary napkin 20 has a main body portion 21 having a periphery 26 which is defined by peripheral seal 25. The longitudinal edges (or "side edges") of the main body portion 21 are designated 22 and the end edges (or "ends") are designated 24, and the corners of the main body portion 21 are designated 27. The main body portion 21 of the sanitary napkin 20 has two end regions, which are designated first end region 28 and second end region 30. A central region 32 is disposed between the end regions 28 and 30. The end regions 28 and 30 extend outwardly from the edges of the central region 32 about 12% to about 33% of the length of the sanitary napkin. A detailed description of a sanitary napkin having a central region 32 and the two end regions 28 and 30 is contained in U.S. Pat. No. 4,690,680, issued to Higgins on Sep. 1, 1987. The main body portion 21 also has a longitudinally oriented middle region 34 and two longitudinally oriented side regions 36. The middle region 34 is bisected by the longitudinal centerline L and is between about 25% and 67% of the lateral width of the main body portion 21 when measured at the transverse centerline T. Preferably, the middle region 34 is greater than about 50% of the lateral width of the main body portion 21 at the transverse centerline T. The side regions 36 extend laterally outward from each side of the middle region 34 to the sides 22 of the main body portion 21. The preferred embodiment of the sanitary napkin 20 shown in FIG. 1 also has a pair of flaps 54 which extend laterally outward from the main body portion 21 along each longitudinal edge 22 thereof in central region 32.

Figure 2:
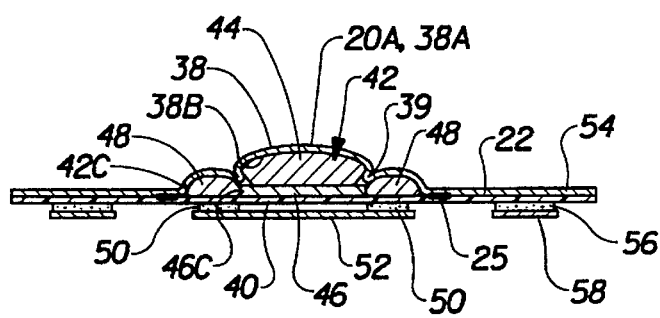
FIG. 2 is an enlarged cross-sectional view of the preferred sanitary napkin embodiment shown in FIG. 1 taken along line 2—2 of FIG. 1.

As can be seen most clearly in FIG. 2, sanitary napkin 20 preferably comprises a liquid pervious topsheet 38, a liquid impervious backsheet 40, an absorbent core 42 positioned between the topsheet 38 and backsheet 40. As is also shown in FIG. 2, the absorbent core 42 comprises three members: an acquisition member 44 which receives bodily discharges that have penetrated through the topsheet 38; a storage/distribution member 46 which draws bodily discharges from the acquisition member 44, distributes them along its longitudinal length, and contains them; and an indicator member 48 which provides a visual signal to a wearer when the absorbent capacity of the sanitary napkin 20 is substantially exhausted. Preferred embodiments of each of these components are discussed in detail below.

2. The Individual Components of the Sanitary Napkin.

A. The Topsheet.

Examining the components of the sanitary napkin in more detail with continuing reference to FIGS. 1 and 2, the topsheet 38 is the component which is oriented towards and contacts the body of the wearer, and receives bodily discharges.

The topsheet 38 is liquid pervious and should be flexible and non-irritating to the skin. As used herein the term "flexible" refers to materials which are compliant and readily conform to the shape of the body or respond by easily deforming in the presence of external forces. The topsheet 38 should exhibit good strike-through and low rewet characteristics, permitting bodily discharges to rapidly penetrate the thickness of the topsheet 38 and move into the acquisition member 44 and sequentially into the storage/distribution member 46, but not flow back through the topsheet 38 to the skin of the wearer. Preferably, the topsheet 38 is not noisy, to provide discretion for the wearer. The topsheet 38 should be sanitary, clean in appearance and somewhat opaque to hide bodily discharges collected in and absorbed by the acquisition member 44 and storage/distribution member 46.

FIG. 2 shows that the topsheet 38 has two sides (or faces or surfaces), including a body-facing side 38A and a garment-facing side (or core-facing side) 38B. The body-facing side 38A of the topsheet 38 generally forms at least a portion of the body-contacting surface ("body surface") 20A of the sanitary napkin 20. The topsheet 38 has, as shown in FIG. 1, two longitudinal edges 38C and two end edges 38D.

A similar numbering system can be used for the other components of the sanitary napkin. That is, the side of the component facing the wearer's body can be designated by the number of the component and a reference letter "A". The side of the component facing the wearer's undergarments can be designated by the number of the component and the letter "B". The side and end edges can be designated by the number of the component and the reference letters "C" and "D", respectively.

A suitable topsheet 38 may be manufactured from a wide range of materials such as woven and nonwoven materials; polymeric materials such as apertured formed thermoplastic films, apertured plastic films, and hydroformed thermoplastic films; porous foams; reticulated foams; reticulated thermoplastic films; and thermoplastic scrims. Suitable woven and nonwoven materials can be comprised of natural fibers (e.g., wood or cotton fibers), synthetic fibers (e.g., polymeric fibers such as polyester, polypropylene, or polyethylene fibers), or from a combination of natural and synthetic fibers.

A preferred topsheet 38 comprises an apertured formed film. Apertured formed films are preferred for the topsheet because they are pervious to body exudates and yet non-absorbent and have a reduced tendency to allow liquids to pass back through and rewet the wearer's skin. Thus, the surface of the formed film which is in contact with the body remains dry, thereby reducing body soiling and creating a more comfortable feel for the wearer. Suitable formed films are described in U.S. Pat. No. 3,929,135, issued to Thompson on Dec. 30, 1975; U.S. Pat. No. 4,324,246 issued to Mullane, et al. on Apr. 13, 1982; U.S. Pat. No. 4,342,314 issued to Radel et al. on Aug. 3, 1982; U.S. Pat. No. 4,463,045 issued to Ahr et al. on Jul. 31, 1984; U.S. Pat. No. 4,629,643 issued to Curro, et al. on Dec. 16, 1986; U.S. Pat. No. 5,006,394 issued to Baird on Apr. 9, 1991; and U.S. Pat. No. 5,342,334, issued to Thompson, et al. on Aug. 30, 1994. Combinations of such formed film topsheets, such as are described in U.S. Pat. No. 5,352,217, issued to Curro on Oct. 4, 1994, are also suitable for the present invention.

Preferably, the topsheet 38 has a plurality of apertures to permit liquids deposited thereon to pass through to the core 42. An apertured polyolefinic film topsheet 38 having about 5 to about 60 percent open area, typically about 25 percent open area, and a thickness of about 0.01 to about 0.05 millimeters prior to aperturing and about 0.42 to about 0.51 millimeters after aperturing is suitable. A particularly suitable topsheet 38 may be made in accordance with U.S. Pat. No. 4,342,314 issued Aug. 3, 1982 to Radel et al. and U.S. Pat. No. 4,463,045 issued Jul. 31, 1984 to Ahr, et al. A topsheet 38 made of model X-3265, model X-8318-8, or model P1552 apertured formed film sold by Tredegar Corporation of Terre Haute, Ind. has been found to work well.

Preferably, the topsheet 38 is sprayed or otherwise treated with a surfactant to enhance liquid penetration to the acquisition member 44 and underlying storage/distribution member 46. Suitable methods for treating the topsheet with a surfactant are described in U.S. Pat. Nos. 4,950,264 and 5,009,653 issued to Osborn. The surfactant is typically nonionic and should be non-irritating to the skin. A surfactant density of about 0.01 milligrams per square centimeter of topsheet 38 area is suitable. A suitable surfactant is sold by Glyco Chemical, Inc. of Greenwich, Conn. as Pegosperse 200 ML.

Alternatively, the topsheet may comprise a fluid-pervious web comprising a first or wearer-contacting surface and a second or garment-facing surface. The first and second surfaces are separated from one another by an intermediate portion. The first surface of the web provides a structure which exhibits a surface energy less than the surface energy of the intermediate portion. In a preferred embodiment, the web exhibits a plurality of regions of comparatively low surface energy which define surface energy gradients where they interface with higher surface energy web surfaces. Webs having such surface energy gradients are fully described in U.S. patent application Ser. No. 08/442,935, filed on May 31, 1995 in the name of Ouellette, et al. the disclosure of which is incorporated herein by reference.

Portions of the topsheet 38 may also comprise a composite topsheet. For example, the apertured formed film located in the middle region 34 may have different properties than the apertured formed film located in the side regions 36. One particularly preferred example of such a composite topsheet comprises a structure having the apertured formed film described in the aforementioned U.S. Pat. No. 4,342,314 located in the middle region 34 and the microapertured polymeric web described in the aforementioned U.S. Pat. No. 4,629,643 positioned in the side regions 36. Such a structure provides a visual signal that absorbed bodily fluids are drawn to the middle of the sanitary napkin 20 that reinforces the visual signal provided by the indicator means 48 (discussed below).

An alternative composite topsheet suitable for the present invention has a central zone and a pair of longitudinally extending side zones that extend laterally outwardly from each side of the central zone. The composite topsheet comprises two layers: a nonwoven layer in both of the side zones and an underlying apertured film layer which lies at least in the central zone. One such composite topsheet is described in U.S. patent application Ser. No. 08/232,242, filed on Nov. 6, 1992 in the name of Sugahara (the disclosure of which is incorporated herein by reference) and published as PCT Application No. WO 93/09744 on May 27, 1993.

Alternative embodiments of the sanitary napkin 20 may also comprise a wipe acquisition layer or secondary topsheet as described in U.S. Pat. No. 4,950,264 issued to Osborn on Aug. 21, 1990 the disclosure of which is incorporated herein by reference. Such a layer serves to provide improved masking of the bodily fluids that are absorbed by the absorbent core 42 and would be positioned between the topsheet 38 and the acquisition layer 44. A suitable material for such a layer is the hydrophilic, thermally bonded, carded polypropylene nonwoven material having a staple denier of less than 2.5 dpf and a basis weight of about 23 grams per square meter (gsm) which is available from the Veratec Division of International Paper, Lewisburg, Pa.

B. The Absorbent Core.

(1) General Properties of the Absorbent Core

The absorbent core 42 is one of the means for collecting and containing bodily discharges, particularly menses, deposited thereon or which otherwise traverse through the liquid permeable topsheet 38. As noted above the absorbent core comprises three members: an acquisition member 44, a storage/distribution member 46, and an indicator member 48, each of which will be described in detail.

The absorbent core 42 may be manufactured in a wide variety of sizes and shapes (e.g., rectangular, oval, hourglass, dog bone, asymmetric, etc.). The absorbent core 42 has a body surface 42A a garment surface 42B, side edges 42C, and end edges 42D. The core 42 is preferably conformable and non-irritating to the skin. The absorbent core 42 of the preferred sanitary napkin 20 shown in FIGS. 1–3 comprises a modified hourglass-shape. As is seen most clearly in FIG. 1, the shape of the absorbent core 42 is defined by the side edges 48C and the end edges 48D of the indicator means 48 and by the end edges 44D of the acquisition member 44.

(2) The Acquisition Member

Figure 3:
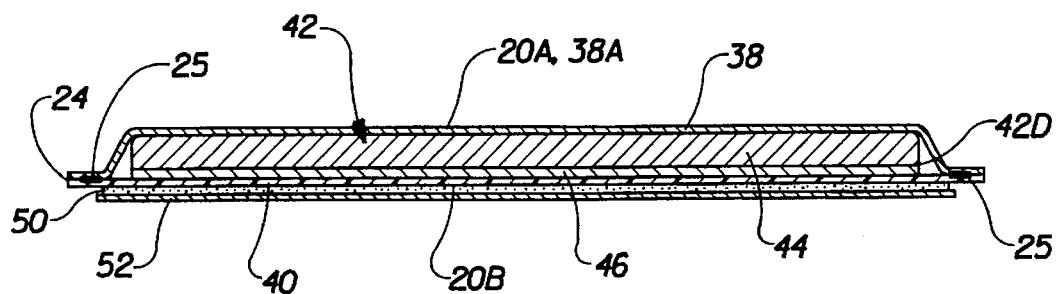
FIG. 3 is a cross-sectional view of the preferred sanitary napkin embodiment shown in FIG. 1 taken along line 3—3 of FIG. 1.

The acquisition member 44, as shown in FIGS. 1–3, is positioned between the topsheet 38 and storage/distribution member 46. The acquisition member 44 is intended to quickly collect and temporarily hold bodily discharges, particularly menses, deposited thereon or which have traversed through the topsheet 38, and transport those bodily discharges to the underlying storage/distribution member 46. A portion of discharged fluid may, depending upon the wearer's position, permeate the acquisition member 44 and be absorbed by the storage/distribution member 46 in the area proximate to the discharge. However, since fluid is frequently discharged at a rate greater than the absorption rate of the storage/distribution member 46, the acquisition member 44 is also capable of drawing absorbed fluid away from the body surface 20A and temporarily containing such fluids until the fluids can be absorbed by the storage/distribution member 46. The fluid handling function of the acquisition member 44 is of particular importance. The acquisition member 44 must have sufficient capillary suction to draw bodily fluids through the topsheet 38 and yet not exhibit excessive fluid retention to make it difficult for the storage/distribution member 46 to desorb the acquisition member 44. The relative fluid handling aspects of the various layers will be discussed more fully below.

The acquisition member 44 is preferably centered along the longitudinal centerline L of the sanitary napkin 20 and is preferably substantially rectangular in plan view. The acquisition member 46 can also either be centered along the transverse centerline, or it can be offset from the transverse centerline (that is, positioned forward or rearward of the transverse centerline). If the acquisition member 46 is offset from the transverse centerline, it is preferably positioned so that it at least partially lies in the central region 32 of the sanitary napkin 20. Preferably, however, as can be seen in FIGS. 1 and 3, the acquisition member extends substantially the entire longitudinal length of the sanitary napkin 20. The acquisition member 44 may have any cross-sectional shape suitable for the design of the sanitary napkin 20. That is, shapes such as square, rectangular, oval (as is shown in FIG. 1), or even an irregular cross section are all suitable.

The acquisition member 44 should have sufficient hiding power to provide a user with confidence that discharges have been "drawn" away from the body surface 20A and into the middle of the sanitary napkin 20. As used herein, the term "hiding power" is intended to mean the ability of a material to minimize the visual impact of absorbed bodily fluids. That is, bodily fluids absorbed by underlying layers of the absorbent core 42 are not substantially visually distinguishable through the preferred embodiment of the acquisition member 44. Typically, the hiding power of a material depends on the opacity of the material. Conversely, the acquisition member 44 should not be so stiff that, when combined with the other members that comprise the absorbent core 42, the sanitary napkin 20 is uncomfortable to a wearer. Thus, as material opacity increases material usage can decrease and as material stiffness decreases material usage can increase. Materials suitable for use as an acquisition member 44 need to provide a suitable balance of opacity and stiffness. For example, if the acquisition member 44 of the present invention comprises comminuted wood pulp, an acquisition member 44 caliper of at least about 12 mm has sufficient opacity to provide the needed hiding power and an acquisition member 44 caliper greater than about 17 mm, when used in combination with the preferred embodiments for the other members comprising the absorbent core 42, begins to be stiff enough to become a potential cause of discomfort. This means that the caliper of this preferred embodiment of the acquisition member 44 is preferably between about 12 mm and about 17 mm. More preferably, the caliper is between about 14 mm and 16 mm. Other materials having opacity and stiffness comparable to a comminuted wood pulp fibrous assembly with this range of caliper would also be suitable for use as an acquisition member 44 as long as the wicking and acquisition rate (discussed elsewhere herein) are also suitable. The caliper measurements should be made at the intersection of the longitudinal centerline L and the transverse centerline T. A suitable method for measuring caliper is given in the Test Methods section below.

The acquisition member 44 is preferably conformable and non-irritating to the skin. In the preferred embodiment shown in FIGS. 1 through 3, the acquisition member 44 is a fibrous assembly. In order that the acquisition member 44 be able to rapidly acquire bodily fluids, it is preferred that the acquisition member 44 have a low density (it is well known in the art that acquisition rate is inversely proportional to structure density). Preferably, the density of the acquisition member 44 is between about 0.04 grams per cubic centimeter (g/cc) and about 0.10 g/cc. More preferably, the density of the acquisition member 44 is between about 0.04 g/cc and about 0.07 g/cc.

In order that the appearance of the body surface 20A of the sanitary napkin 20 remains relatively clean throughout the useful life of the sanitary napkin 20, the acquisition member 44 should have low wicking potential (i.e., the structure of the acquisition member 44 should be designed to enable fluid transfer to the storage/distribution member 46 rather than to wick fluids through its volume). Materials having a vertical wicking height of less than about 7 centimeters for the artificial menstrual fluid (AMF) that is described in the TEST METHODS section below have been found to have suitably low wicking potential. A method for measuring vertical wicking height is also described in the Test Methods section below.

Suitable fibrous materials for the acquisition member 44 include, but are not limited to, cross-linked cellulose fibers, synthetic staple fibers, polymeric fibers or any equivalent materials or combination of materials. Such fibers can be formed into a fibrous assembly using means well known in the art such as carding, air laying, spun bonding, and melt blowing. In the preferred embodiment shown in FIGS. 1, 2, and 3, the acquisition member comprises an air laid fibrous assembly of comminuted wood pulp (which is generally referred to as airfelt).

The acquisition member 44 must be in effective fluid communication with the topsheet 38 (or other overlying layer, such as a wipe acquisition layer) and may be joined thereto. As used herein, the term "effective fluid communication" is intended to mean that bodily fluids can be transferred between two elements of the sanitary napkin by capillary or other means. Preferably, the acquisition member 44 is in close contact with or attached to the topsheet 38. This will facilitate the transport of bodily exudates through the topsheet 38 (i.e., the acquisition member 44 will draw exudates through the top sheet 38) due to the higher capillarity of the acquisition member 44. The acquisition member 44 can be joined to the overlying component in any suitable manner, including but not limited to adhesives, such as hot melt adhesives, heat and/or pressure bonds, ultrasonic bonds, or any of the other manners known to the art. Preferably, the acquisition member 44 is joined to the top sheet by an open pattern network of filaments comprising several lines of adhesive filaments swirled into a spiral pattern such as illustrated by the apparatus and method shown in U.S. Pat. No. 3,911,173 issued to Sprague, Jr. on Oct. 7, 1975; U.S. Pat. No. 4,785,996 issued to Ziecker, et al. on Nov. 22, 1978; and U.S. Pat. No. 4,842,666 issued to Werenicz on Jun. 27, 1989. The disclosure of each of these patents is incorporated herein by reference. Alternatively, the acquisition member 44 may be unattached to the topsheet.

The acquisition member 44 must also be in effective fluid communication with the storage/distribution member 46. The acquisition member 44 and the storage/distribution member 46 may be unattached or, preferably, the acquisition member 44 is joined to the storage/distribution member 46 using means similar to those used to join the acquisition member 44 and the topsheet 38.

The acquisition member 44 can also comprise a foam material having the requisite capillary properties. A suitable foam material can be prepared using High Internal Phase Emulsion (HIPE) technology. Suitable HIPE foams have a hole size of between about 8 microns and about 20 microns so as to not filter erythrocytes from bodily fluids, such as menstrual discharges, so that the foam becomes clogged. Such HIPE foams are described in U.S. patent application Ser. No. 08/370,697, filed in the name of Dyer on Jan. 10, 1995 the disclosure of which is incorporated herein by reference.

(2) The Storage/Distribution Member

The storage/distribution member 46, as is shown in FIGS. 1–3, is a structure that is positioned below the acquisition member 44. The storage/distribution member 46 serves a dual purpose, both containing those bodily fluids it receives and also directing the received fluids along its longitudinal length distributing them to fully utilize its storage capacity so as to minimize the amount of fluid contained in other portions of the core 42. That is, the storage/distribution member 46 preferably stores absorbed fluids in the middle portion 34 of the main body portion 21.

As is shown in FIGS. 1 and 3, the storage/distribution member 46 is preferably centered on the longitudinal centerline L and the transverse centerline T and runs substantially the entire longitudinal length of the sanitary napkin 20. The remaining two dimensions must be such that, when the absorbent capacity of the absorbent core 42 is considered, the storage/distribution member 46 possesses sufficient volume to provide a satisfactory useful life to the sanitary napkin 20. Preferably, the lateral width of the storage/distribution member 46 is between about 25% and about 67% of the lateral width of the main body portion 21 at the transverse centerline T. More preferably, the storage/distribution member 46 is at least about 50% of the lateral width of the main body portion 21 measured at the transverse centerline T. The storage/distribution member 46 should preferably be as thin as possible, in keeping with the storage capacity requirements thereof, in order to maximize the flexibility of the sanitary napkin 20.

The storage/distribution member 46 may be joined to underlying components of the sanitary napkin using means familiar to those skilled in the art. For example, the storage/distribution member 46 may be joined to underlying structure by a uniform continuous layer of adhesive, a patterned layer of adhesive, or an array of separate lines, spirals, or spots of adhesive. Adhesives which have been found to be satisfactory are manufactured by the H. B. Fuller Company of St. Paul, Minn. under the designation HL-1258. The attachment means will preferably comprise an open pattern network of filaments of adhesive as is disclosed in U.S. Pat. No. 4,573,986 which issued to Minetola, et at. on Mar. 4, 1986, and the disclosure of which is incorporated herein by reference. An exemplary attachment means of an open pattern network of filaments comprises several lines of adhesive filaments swirled into a spiral pattern such as illustrated by the apparatus and method shown in U.S. Pat. No. 3,911,173 issued to Sprague, Jr. on Oct. 7, 1975; U.S. Pat. No. 4,785,996 issued to Ziecker, et at. on Nov. 22, 1978; and U.S. Pat. No. 4,842,666 issued to Werenicz on Jun. 27, 1989. Each of these patents are incorporated herein by reference. Alternatively, the attachment means may comprise heat bonds, pressure bonds, ultrasonic bonds, dynamic mechanical bonds, or any other suitable attachment means or combinations of these attachment means as are known in the art.

One key purpose of the storage/distribution member 46 is to receive bodily fluids from the acquisition member 44 and store them in a location that is away from the body surface 20A of sanitary napkin 20. That is, the storage/distribution member 46 "draws" bodily fluids from the acquisition member 44 into its structure and stores them therein. Preferably, such fluids are drawn in the "Z"-direction (i.e. the direction perpendicular to the plane of the sanitary napkin 20) from the acquisition member 44 into the storage/distribution member 46 so that the amount of bodily fluid that is readily visible on the body surface 20A of the sanitary napkin 20 is minimized. It has been found that capillary suction for the storage/distribution member 46 should be higher than the capillary suction of the acquisition member 44 if the storage/distribution member 46 is to draw bodily fluids in the "Z"-direction from the acquisition member 44. While capillary suction can be defined in several ways (e.g., pore size, density, basis weight, etc.), vertical wicking height is the preferred parameter for defining the relative capillary suction difference between the acquisition member 44 and the storage/distribution member 46. Thus, if the acquisition member 44 and the storage/distribution member 46 comprise fibrous structures, the storage/distribution member 46 should have a higher average vertical wicking height in order to draw fluids from the acquisition member 44. Preferably, the ratio of the vertical wicking height of the storage/distribution member 46 to the vertical wicking height of the acquisition member 44 should be about equal to or greater than about 1.5:1, more preferably equal to or greater than about 2:1. For example, the particularly preferred wet laid, tri-component members described below have vertical wicking heights between about 16 cm and about 28 cm for AMF when measured as described in the TEST METHODS section. If such materials are used for the storage/distribution member 46, the resulting wicking height ratio for an acquisition member 44 having a 7 cm vertical wicking height would be between about 2.3:1 and about 4:1.

The total absorbent capacity of the storage/distribution member 46 should, however, be compatible with the design loading and the intended use of the sanitary napkin 20. That is, the storage/distribution member 46 should be designed to provide substantially the entire absorbent capacity of the absorbent core 42 in order that a user will recognize that, when the indicator member 48 begins to become visibly soiled, the risk of leakage along the longitudinal edges 26 has substantially increased and that it is time to change sanitary napkins. Further, the size and absorbent capacity of the storage/distribution member 46 may be varied to accommodate different uses such as incontinence pads, pantiliners, regular sanitary napkins, or overnight sanitary napkins.

The storage/distribution member 46 also directs absorbed bodily fluids such as blood, menses and urine received from the storage/distribution member 46 towards the ends 42D of the absorbent core 42. The storage/distribution member 46 can direct bodily discharges laterally, but it preferably does not direct such discharges all the way to the side edges 46C of the storage/distribution member 46. Rather, the storage/distribution member 46 is intended to preferentially distribute bodily exudates toward the ends 24 of the sanitary napkin 20. The exudates are preferably distributed so that exudates will not reach the side edges 26 of the sanitary napkin 20 at least until exudates are transported so as to substantially use any available absorbent capacity in the end regions 28, 30 of sanitary napkin 20.

As noted above, the preferred storage/distribution member 46 of the present invention has capillary properties that function to draw bodily fluids from the acquisition member 44. A storage/distribution member 46 having such capillary properties may be manufactured from a wide variety of liquid-absorbent materials commonly used in sanitary napkins and other absorbent articles such as comminuted wood pulp which is generally referred to as airfelt. Examples of other suitable absorbent materials include meltblown polymers including coform; chemically stiffened, modified or cross-linked cellulosic fibers; synthetic fibers such as crimped polyester fibers; peat moss; tissue including tissue wraps and tissue laminates; absorbent foams; absorbent sponges; superabsorbent polymers; absorbent gelling materials; porous, absorbent, polymeric macrostructures; or any equivalent material or combinations of materials, or mixtures of these. Preferably, the storage/distribution member 46 comprises a fibrous assembly having the requisite capillary properties. Such fibrous assemblies can be provided with the requisite capillary properties by providing them with the vertical wicking height as described above such as providing a fibrous assembly with a desired basis weight and then densifying it to provide the requisite vertical wicking height. Suitable fibrous assemblies are the thermally bonded, air laid assemblies described in U.S. patent application Ser. No. 08/141,156 filed on Oct. 21, 1993 in the name of Richards, et al. (allowed, no number assigned; published as PCT Application No. WO 95/10996).

A still more preferred fibrous assembly for the storage/distribution member 46 of the present invention comprises the wet laid, tri-component members described in copending U.S. patent application Ser. No. 08/382,817, filed on Feb. 3, 1995 in the name of Horney, et al. the disclosure of which is incorporated herein by reference. As described therein, this preferred fibrous assembly comprises from about 20% to about 80% chemically stiffened, twisted, and curled fibers as described in U.S. Pat. No. 4,822,453, issued to Dean, et al. on Apr. 18, 1989, U.S. Pat. No. 4,888,093, issued to Dean, et al. on Dec. 19, 1989, U.S. Pat. No. 4,898,642, issued to Moore, et al. Feb. 6, 1990, and U.S. Pat. No. 5,183,707 issued to Herron, et al. on Feb. 2, 1993, the disclosure of each of these patents is incorporated herein by reference; from about 10% to about 80% of a high surface area fiber, such as eucalyptus wood pulp fibers; and from 0% to about 50% of a thermoplastic binding means for increasing the physical integrity of the web. All percentages herein refer to weight percentages based on total dry web weight. Preferably, the fibrous assembly will comprise between about 45% and about 60% of chemically stiffened, twisted, and curled fibers, between about 5% and about 15% of a hot melt fibrous binding means, and between about 30% and about 45% high surface area cellulose fibers. More preferably, the fibrous assembly comprises about 10% thermoplastic binding means, about 60% chemically stiffened, twisted, and curled fibers, and about 30% high surface area fibers. Chemical additives can also be used as binding means, and are incorporated into the acquisition/distribution layer at levels typically of about 0.2% to about 2.0%, on a dry web weight basis. Suitable fiber types for each component of this preferred fibrous assembly are listed in the aforementioned U.S. patent application Ser. No. 08/382,817.

In alternative embodiments of the present invention materials which retain bodily fluids using osmotic means, such as superabsorbent polymers, absorbent gelling materials, or the like, can be provided between the storage/distribution member 46 and the backsheet 40 or the storage/distribution member 46 can further comprise end portions lying in the end regions 28 and 30 of the sanitary napkin 20 wherein the end portions comprise a mixture of a fibrous material with such osmotic retention materials. Alternative embodiments of this type have the further advantage of containing absorbed fluids not just by capillary means but also by the swelling of such osmotic absorbent means.

In a second alternative embodiment of the present invention the storage/distribution member 46 can comprise a foam material having the requisite capillary properties. Suitable foam materials are described in U.S. Pat. No. 5,318,554, issued to Young, et al. on Jun. 7, 1994 and in the aforementioned U.S. patent application Ser. No. 08/370,697 the disclosure of which is incorporated by reference (3) The Indicator Member The indicator member 48 provides the user with a visual signal that the sanitary napkin 20 is approaching its designed capacity and that it is time to change. The signal is provided by designing the relative capillarity of the storage/ distribution member 46 and the indicator member such that the indicator member 48 does not begin to absorb bodily fluids (i.e. become noticeably visibly stained) until the absorbent capacity of the storage/distribution member is substantially exhausted. As noted above, the storage/ distribution member 46 is designed to have a combination of density and basis weight that provide it with capillary properties that preferentially draw bodily fluids from the acquisition member 44. Thus, it is preferable that the indicator member 48 have capillarity (i.e., density and vertical wicking height) that is similar to that of the acquisition member 44 to insure that indicator member 48 does not begin to absorb bodily fluids until the absorbent capacity of the storage/distribution member 46 is substantially exhausted. With such a relationship between the relative capillarities, the indicator member 48 would not begin to absorb bodily fluids until the absorbent capacity of the storage/distribution member 46 is substantially exhausted and, if the absorbent capacity of the storage/distribution member 46 is not substantially exhausted, the relative capillarities would tend to cause the storage/distribution member 46 to draw any bodily fluids that may be inadvertently deposited on the indicator member 48 into the middle region 34 of the main body portion 21 and away from the indicator member 46.

Figure 4:
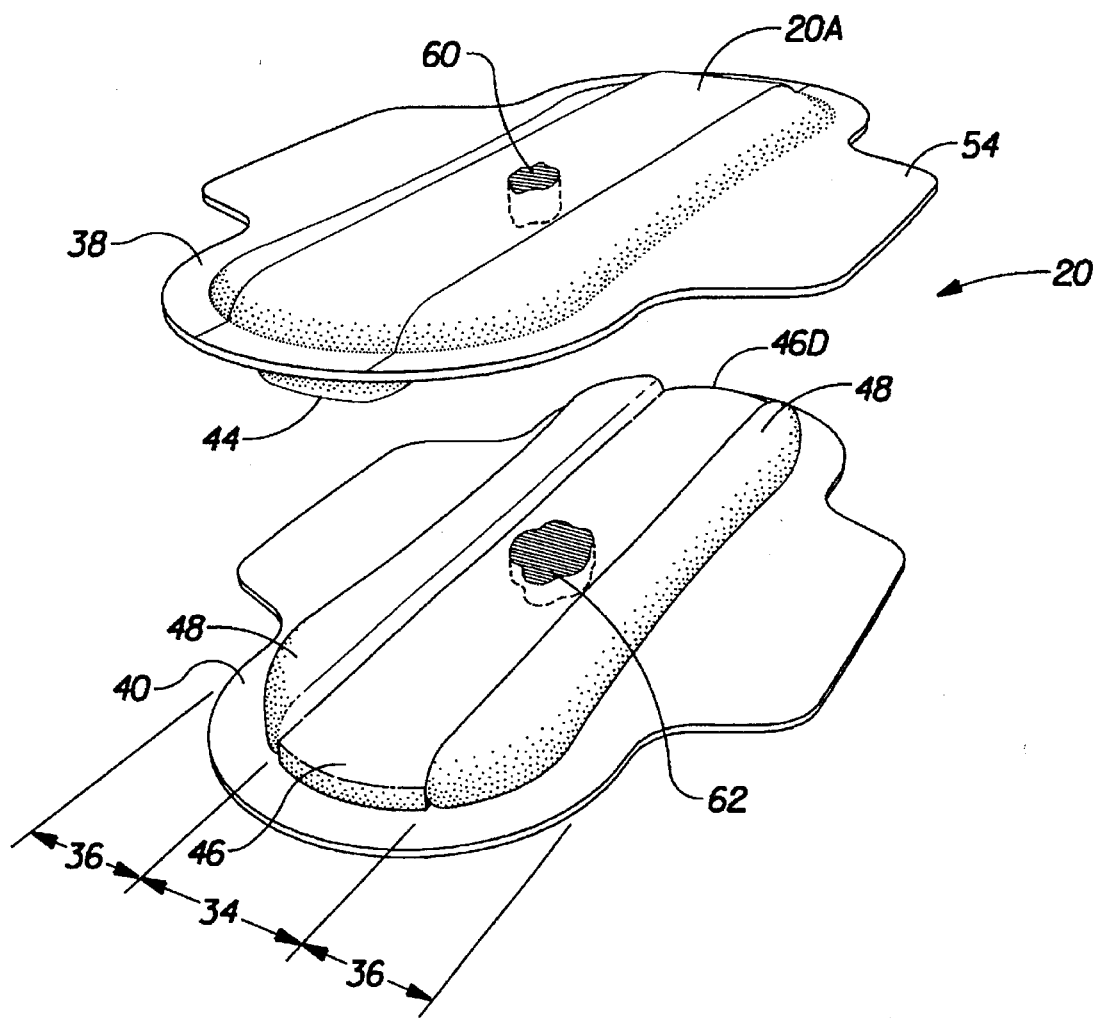
FIG. 4 shows a diagrammatic representation of a sanitary napkin of the present invention early in a simulated (by "titration" with artificial menstrual fluid) wear cycle. The absorbent core has been separated along a plane between the acquisition member and the storage/distribution member thereof to show the partitioning of the artificial menstrual fluid between the members which comprise the core.
Figure 5:
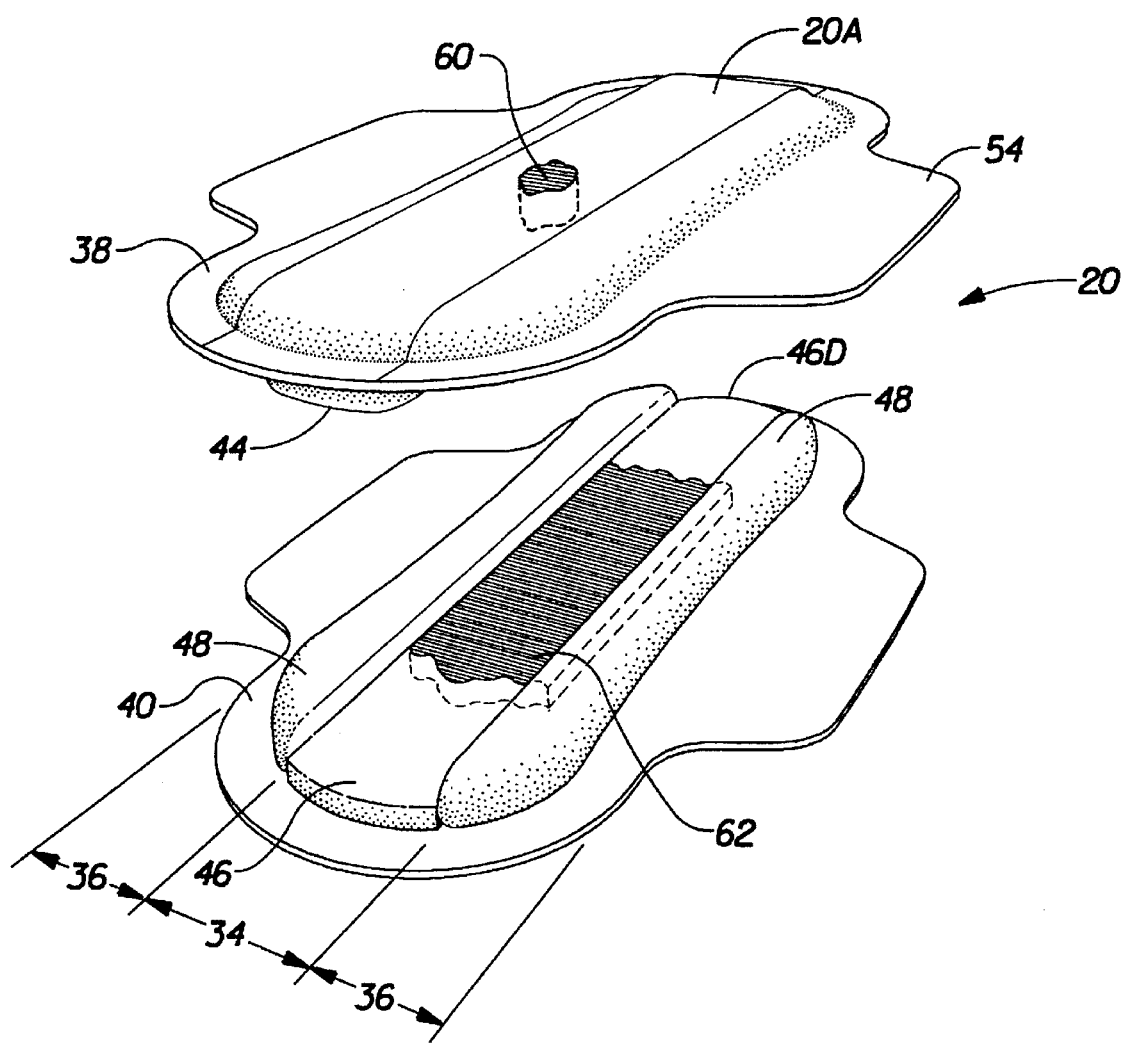
FIG. 5 is similar to FIG. 4 and shows the partitioning of the artificial menstrual fluid later in the wear cycle.
Figure 6:
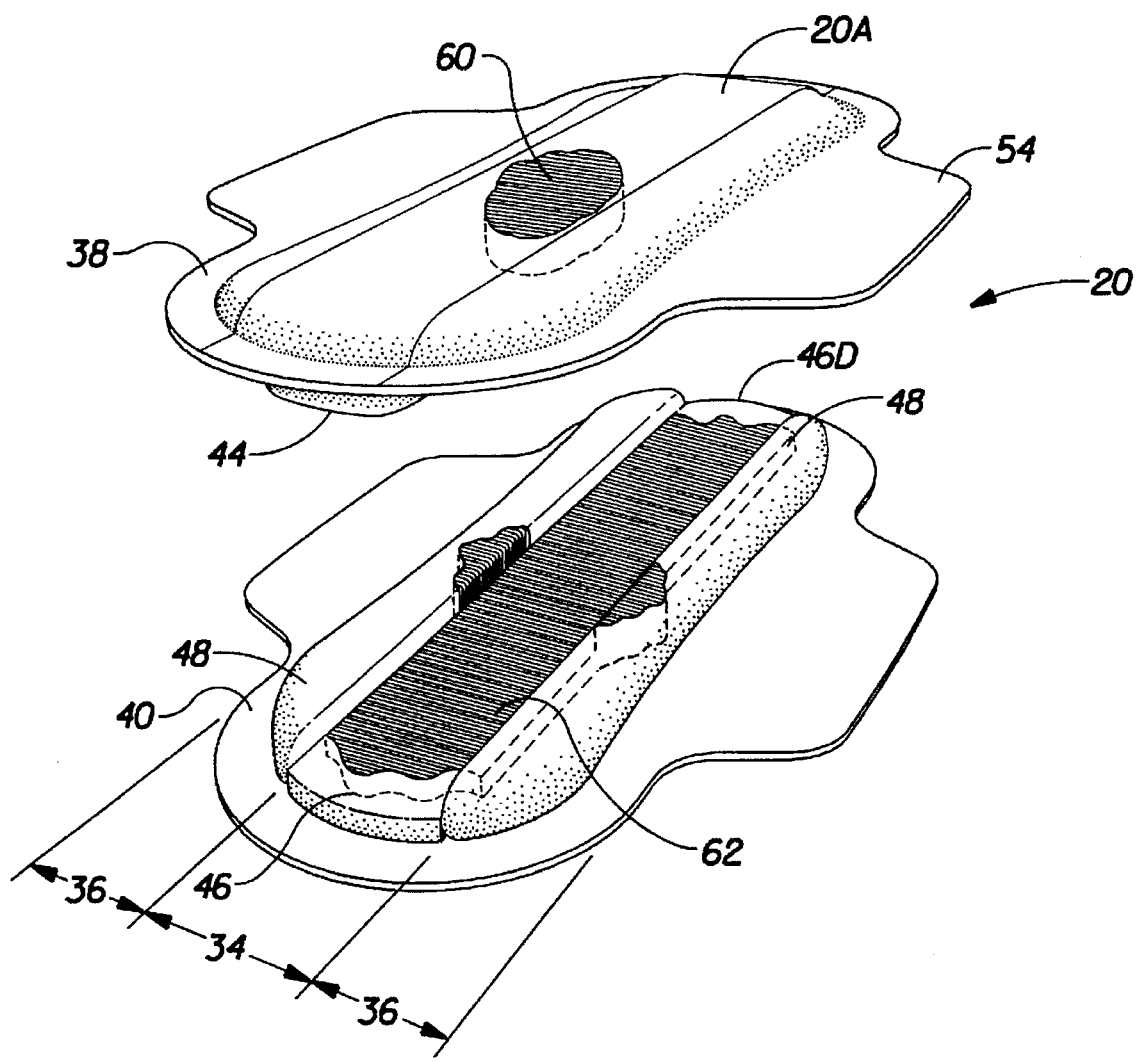
FIG. 6 is also similar to FIGS. 4 and 5 and shows the partitioning of the artificial menstrual fluid near the end of the wear cycle when the absorption capacity of the sanitary napkin is substantially exhausted.

FIGS. 4 to 6 diagrammatically illustrate how the three components of the absorbent core 42 are intended to cooperate to insure that absorbed bodily fluids remain in the middle region 34 for the bulk of the wear cycle of the sanitary napkin 20. FIGS. 4 to 6 further diagrammatically show how the indicator means 48 is designed to provide a visual signal when the absorbent capacity of the storage/ distribution member 46 is substantially exhausted indicating that it is time to change. This series of figures is based on a "titration" of the preferred embodiment of the sanitary napkin 20 that is shown in FIGS. 1 to 3 at a rate of 2 milliliters per hour with AMF up to its absorbent capacity, simulating loading of the sanitary napkin over its wear cycle. FIG. 4 represents the condition of the sanitary napkin 20 as it would appear early in the wear cycle. At this stage the sanitary napkin 20 has absorbed about ten percent of its design capacity for AMF. As used herein the term "design capacity" is intended to mean the absorbent capacity that is provided to sanitary napkin 20 of the present invention to insure that it has a useful wear cycle. Sanitary napkins of the present art typically have a design capacity of between about 20 grams and about 40 grams. As is clear shown by the "stain" patterns 60, 62 in FIG. 4, the bulk of the absorbed fluid is located in the middle region 34 of the main body portion 21, well away from the side regions 36. FIG. 4 also shows how the AMF is drawn from the surface, through the acquisition member 44 into the storage/distribution member 46 (the "stained" portion 60 of the acquisition member 44 is smaller than the "stained" portion 62 of the storage/ redistribution member 46.). Such drawing from the surface helps the body surface 20A maintain a clean/dry appearance. FIG. 5 represents the middle stage of the wear cycle where the sanitary napkin 20 has absorbed about thirty percent of its theoretical capacity for the AMF. As can be seen from the "stained" portion 62 of the storage/distribution member 46, the additional fluid is distributed mainly in the longitudinal direction and is substantially contained in the middle region 34. The "stained" portion 60 of the acquisition member 44 continues to demonstrate how the AMF is drawn from the surface. FIG. 6 shows the appearance of the sanitary napkin 20 when the absorbent capacity of the storage/distribution member 46 is substantially exhausted. As can be seen therein, the "stain" 62 is approaching the longitudinal ends 46D of the storage/distribution member 46 and has begun to spread into the side regions 36. This spreading into the side regions 36 provides the signal that the capacity is substantially exhausted and that it is time to change.

As shown most clearly in FIG. 2, the indicator member 48 is in effective fluid communication with the topsheet 38 and with the storage/distribution member 46. This means that any bodily fluids that inadvertently are deposited on the topsheet 38 in a side region 36 would be drawn away from the topsheet 38 in the same manner as the acquisition member 44 draws fluids away from the topsheet 38 and that the storage/distribution member 46 would draw such fluids from the indicator member 48 into the middle region 34. This also means that the indicator member 48 can receive bodily fluids from the storage/distribution member 46 when the absorbent capacity thereof has been substantially exhausted so as to provide a signal of the need to change the sanitary napkin 20.

The indicator member 48 may be joined to the topsheet 38 (or other overlying layer) and or the backsheet 40 using means familiar to those skilled in the art as described above with respect to the acquisition member 44. Preferably the indicator member 48 is joined to the topsheet 38 and the backsheet 40 using means essentially the same as those used to join the acquisition member 44 to the topsheet 38 and to the storage/distribution member 46. That is, the indicator member 48 is preferably joined to the topsheet 38 and the backsheet 40 by an open pattern network of filaments comprising several lines of adhesive filaments swirled into a spiral pattern.

As is shown most clearly in FIG. 1, indicator member 48 preferably comprises two spaced apart portions, one portion defining each of the side regions 36 and the general shape of the absorbent core. As can be seen therein the edges 48C that are adjacent to the sides 22 have an inwardly arcuate shape in central region 32 and an outwardly arcuate shape in the first and second end regions 28, 30, providing the absorbent core 42 with a modified hour glass shape. The opposite longitudinal edge of each indicator member 48 is juxtaposed with the longitudinal edge of the storage/distribution member 46. As can also be seen, each indicator member 48 extends substantially the entire longitudinal length of the sanitary napkin 20. The cross section of the indicator member 48 is shown to be oval in FIG. 2, although other cross sections such as square, rectangular or an irregular cross section are also suitable. Importantly, the caliper of the indicator member 48 should preferably be less than the combined calipers of the storage/distribution member 46 and the acquisition member 44 so as to provide a user with a visual indication that the absorbent capacity of the sanitary napkin 20 is concentrated in the middle region 34. Preferably, the caliper of the indicator member 48 is between about 30% and about 60% of the combined calipers of the storage/distribution member 46 and the acquisition member 44. To further provide a visual indication that the absorbent capacity is concentrated in the middle region 34, the topsheet 38 is provided with a "pleat" 39 along the line of juxtaposition between the acquisition member 44 and the indicator member 48, which lies along side edge 44C of the acquisition member in FIG. 1.

As noted above, the indicator member 48 preferably has similar capillarity to the acquisition member 44. This means that materials and properties that are suitable for the acquisition member 44 are also suitable for the indicator member 48. As such, the preferred indicator member 48 shown in FIGS. 1 and 2 comprises an air laid fibrous assembly of comminuted wood pulp (which is generally referred to as airfelt). Preferably the density of the fibrous assembly comprising the indicator member 48 is between about 0.04 g/cc and about 0.10 g/cc, more preferably between about 0.04 g/cc and about 0.07 g/cc and the vertical wicking height is less than about 7 centimeters for AMF. This difference in capillarity sets up a laterally directed capillary gradient between the indicator member 48 and the storage/distribution member 46 that causes absorbed bodily fluids to be retained primarily in the storage/distribution member 46 until the capacity thereof is substantially exhausted. The indicator member 46 then begins to absorb bodily fluids, becoming stained as described above and providing the visual signal that it is time to change the sanitary napkin 20.

Figure 7:
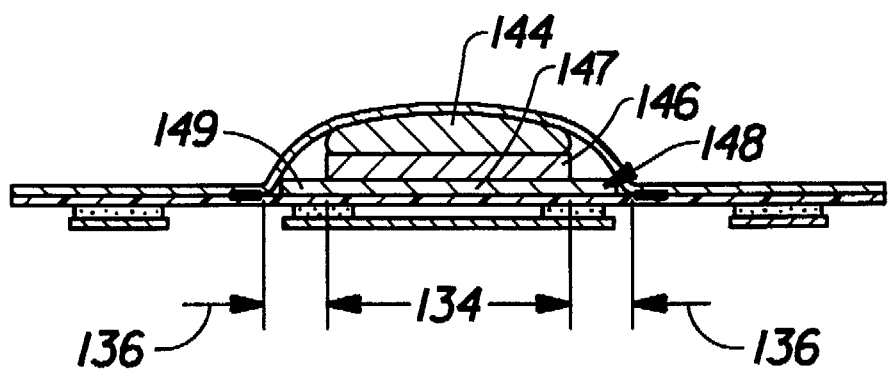
FIG. 7 is an enlarged cross-sectional view, similar to FIG. 2, of an alternative embodiment of the present invention.

In the alternative embodiment of the present invention, sanitary napkin 120, shown in FIG. 7, a portion of the indicator member 148 is positioned between the storage/distribution member 146 and the backsheet 140. In this embodiment a portion 147 of the indicator member 148 lies in the middle region 134 and a portion 149 lies in each of the side regions 136. Such an embodiment of the present invention would be suitable for those users who prefer a thicker sanitary napkin.

C. The Backsheet.

The backsheet 40 prevents the exudates absorbed and contained in the absorbent core 42 from wetting articles which contact the sanitary napkin 20 such as pants, pajamas and undergarments. The backsheet 40 is impervious to bodily fluids (e.g., menses and/or urine). The backsheet 40 is preferably manufactured from a thin plastic film, although other flexible liquid impervious materials may also be used.

The backsheet 40 may comprise a woven or nonwoven material, polymeric films such as thermoplastic films of polyethylene or polypropylene, or composite materials such as a film-coated nonwoven material. Preferably, the backsheet 40 is a polyethylene film having a thickness of from about 0.012 mm (0.5 mil) to about 0.051 mm (2.0 mils). Exemplary polyethylene films are manufactured by Clopay Corporation of Cincinnati, Ohio, under the designation P18-1401 and by Tredegar Film Products of Terre Haute, Ind., under the designation XP-39385.

The backsheet 40 is preferably embossed and/or matte finished to provide a more clothlike appearance. Further, the backsheet 40 may permit vapors to escape from the absorbent core 42 (i.e., the backsheet 40 may be breathable) while still preventing exudates from passing through the backsheet 40. Flushable or biodegradable backsheets can also be used, e.g., such as with the pantiliner devices described herein.

D. Flaps

The preferred embodiment of the sanitary napkin 20 shown in FIGS. 1–3 is also provided with a pair of flaps 54, each of which is adjacent to and extends laterally outward from a side edge 22 of the main body portion 21 of the sanitary napkin in the central region 32 (The main body portion 21 is the portion of the sanitary napkin without the flaps and is defined by the peripheral seal 25.) The flaps 54 are preferably configured to drape over the edges of the wearer's panties in the crotch region so that they are disposed between the wearer's panties and the wearer's thighs.

Such flaps can serve at least two purposes. First, the flaps 54 help to prevent soiling of the wearer's body and panties by menstrual fluid or other bodily exudates. Second, the flaps 54 are preferably provided with flap attachment means 56 on their garment surface so that the flaps 54 can be folded back under the panty and attached to the garment-facing side of the panty. In this way, the flaps 54 serve to keep the sanitary napkin 20 properly positioned in the panty. Alternatively, the flaps 54 may be attached to each other on the underside of the panty by the attachment means 56 with or without also being affixed to the panty.

A number of sanitary napkins having flaps suitable or adaptable for use with the sanitary napkin 20 of the present invention are known. Such flaps are disclosed in U.S. Pat. No. 4,285,343, issued to MeNair on Aug. 25, 1981; U.S. Pat. No. 4,589,876, issued to Van Tilburg on May 20, 1986; U.S. Pat. No. 4,608,047, issued to Mattingly on Aug. 26, 1986; U.S. Pat. No. 4,687,478 issued to Van Tilburg on Aug. 18, 1987; and in Reexamination Patent B14,589,876 issued Apr. 27, 1993. Some particularly preferred types of flaps are described in U.S. Pat. No. 5,281,209 issued to Osborn, et al. on Jan. 25, 1994; in U.S. Pat. No. 5,344,416 issued to Lavash, et al. on Sep. 6, 1994; and in U.S. Pat. No. 5,354,400 issued to Lavash, et al. on Oct. 11, 1994.

The flaps 54 can be constructed of various materials including tissue, woven or nonwoven materials, materials similar to the topsheet 38, the backsheet 40, or any combination of these materials. Further, the flaps 54 may be a separate dement attached to the main body of the sanitary napkin 20 or can comprise extensions of the topsheet 38 and backsheet 40 (i.e., unitary). Preferably, as is shown most clearly in FIG. 2, the flaps 54 comprise extensions of the topsheet 38 and the backsheet 40. The extended top sheet 38 and backsheet 40 are joined using means familiar to those skilled in the art. Preferably, the extended topsheet 38 and backsheet 40 are joined by an adhesive.

E. Fasteners for Attaching the Sanitary Napkin to the Wearer's Panties

The outwardly-oriented face of the backsheet 40 may, as shown in FIGS. 1 and 2, further comprise a means for attaching the sanitary napkin 20 to the undergarment of the wearer, such as fastening means 50 and flap attachment means 56.

Attachment means (i.e., fastening means 50 and flap attachment means 56) comprising adhesives have been found to work well for this purpose. Any adhesive or glue used in the art for such purposes can be used, with pressure-sensitive adhesives being preferred. Suitable adhesives are Century A-305-IV manufactured by the Century Adhesives Corporation of Columbus, Ohio, Instant Lock 34-2823 manufactured by the National Starch Company of Bridgewater, N.J., and Fuller HL-2238ZP manufactured by the H. B. Fuller Co. of St. Paul, Minn. Suitable adhesive fasteners are also described in U.S. Pat. No. 4,917,697.

The fastening means 50 can be in many possible configurations depending on the characteristics desired for the sanitary napkin. FIG. 2 shows one preferred arrangement which utilizes two longitudinally oriented strips of adhesive, one on each side of the longitudinal centerline L. Particularly suitable fastener configurations are shown in PCT Publication No. WO 92/04000 published in the name of Papa, et al. on Mar. 19, 1992. Flap attachment means 56 can also be disposed in many configurations, including oval, rectangular, square, or any other configuration dictated by the particular design of the flap 54. In the preferred embodiment shown in FIGS. 1 and 2, the flap attachment means 56 are disposed in a rectangular pattern near the distal edge of each flap.

In addition, other types of fasteners can be used instead of, or in addition to adhesives. These other types of fasteners are preferably arranged in patterns similar to those in the patent publications referred to above. Such fasteners include, but are not limited to conventional VELCRO hook material, the fasteners described in: U.S. Pat. No. 4,946,527 issued to Battrell on Aug. 7, 1990; U.S. Pat. Nos. 5,058,247 and 5,116,563 issued to Thomas, et al. on Oct. 22, 1991 and May 26, 1992, respectively; and U.S. Pat. No. 5,318,741 issued to Thomas on Jun. 7, 1994; or, high coefficient of friction foams and other high coefficient off fiction materials.

Before the sanitary napkin 20 is placed in use, if an adhesive fastener is used, the fastening means 50 is typically covered with a removable cover strip or release liner 52 in order to keep the adhesive from sticking to a surface other than the crotch portion of the panty prior to use. Similarly, the flap attachment means 56 is covered with flap release liner 58. Suitable release liners are also described in the above-referenced U.S. Pat. No. 4,917,697. Any commercially available release liners commonly used for such purposes can be utilized herein. Non-limiting examples of suitable release liners are BL30MG-A Silox E1/0 and BL25MG-A Silox 4R/0, both of which are manufactured by the Akrosil Corporation of Menasha, Wis.

In one particularly preferred embodiment, the fastening means 50 is protected with a wrapper that not only covers the adhesive, but also provides both an individually packaged sanitary napkin and a container for disposing the sanitary napkin after use, such as is described in U.S. Pat. No. 4,556,146 issued to Swanson, et al. on Dec. 3, 1985.

The sanitary napkin 20 of the present invention is used by removing any release liner 52, 58 and thereafter placing the sanitary napkin 20 in a panty so that the fastening means 50 contacts the panty on its body facing surface, the flaps 54 drape over the edges of the panty leg openings and the flap attachment means 56 contact the panty on its garment facing surface, maintaining the sanitary napkin in position within the panty during use.

F. Assembly of the Components of the Sanitary Napkin. The components of the sanitary napkin such as the topsheet, the backsheet, the absorbent core, and any other components, may be assembled in a variety of well known configurations (including so called "tube" products or side flap products). The components of the sanitary napkin are preferably assembled in a "sandwich" configuration with the topsheet, backsheet, and absorbent core each comprising a layer and the absorbent core positioned between the topsheet and backsheet. The topsheet 38 and the backsheet 40 are preferably peripherally joined by peripheral seal 25 using known techniques. The topsheet 38 and backsheet 40 can be joined either entirely peripherally so that the entire periphery 26 of the main body portion 21 and the edges of the flaps 54 is circumscribed by the joinder of the components, or these two components can be only partially peripherally joined at the perimeter. In the preferred embodiment shown in FIGS. 1–3, the topsheet 38 and the backsheet 40 are joined about the entire periphery 26 by peripheral seal 25 and about the edges of the flaps 54.

The components of the sanitary napkin 20 can be secured together by adhesives, stitching, heat and/or pressure bonds, dynamic mechanical bonds, ultrasonic bonds, intermingling or entanglement of the fibers or other structural elements comprising the components of the sanitary napkin, such as by meltblowing the fibers comprising one component onto another component, extruding one component onto another, or by any other means known in the art.

F. Alternative Embodiments and Optional Features.

(1) Lifting Members

Lifting members are one means that the art has used to provide for improved body contact for sanitary napkins. As used herein, the term "lifting member" is intended to mean an element of the structure of a sanitary napkin that is intended to provide "Z"-direction height to the sanitary napkin in order to improve body contact. One type of lifting member is described in U.S. patent application Ser. No. 08/225,405, filed in the name of McFall on Apr. 8, 1994 and published as PCT Application WO 95/17150 on Jun. 29, 1995. Described therein is a longitudinally extending lifting member, the lifting member having a plurality of pleats which have a "Z"-direction height. The lifting member is preferably disposed between the core and the backsheet of a sanitary napkin along the longitudinal centerline thereof and provides "Z"-direction elastic displacement of a portion of the topsheet relative to the backsheet causing it to take a convex upward shape for improved body contact. A second type of lifting member is described in U.S. patent application Ser. No. 08/225,411, filed in the name of Bergman on Apr. 8, 1994 and published as PCT Application WO 95/17149 on Jun. 29, 1995. This lifting member is a filament spring that is disposed between the core and the backsheet. The spring provides elastic displacement of the top sheet relative to the backsheet and convexly shapes the body facing surface of the topsheet. Yet another type of lifting member is described in U.S. Pat. No. 5,300,055, issued to Buell of Apr. 5, 1994. This lifting member is a flexure-resistant deformation element. The deformation element relies on the lateral compressive forces of a wearer's thighs to create and maintain a convex upward configuration when a sanitary napkin comprising such a member is worn. Yet a third type of lifting member suitable for the present invention can comprise an assembly of moisture insensitive fibers that is disposed between the topsheet and the backsheet. As used herein, the term "moisture insensitive fibers" is intended to describe fibrous assemblies that substantially maintain their structural integrity when exposed to bodily fluids. For example a tow of moisture insensitive fibers, such as polyester fibers, can be disposed beneath at least a portion of the storage/distribution member 46 of the present invention to provide additional caliper to the sanitary napkin such that the storage/distribution member 46 and the overlying acquisition member 44 have improved bodily contact. Since such a lifting member is comprised of moisture insensitive fibers, it helps to maintain such improved bodily contact for substantially the entire wear cycle of the sanitary napkin. These and other types of lifting members are all suitable or adaptable for use with the sanitary napkin 20 of the present invention as long as the lifting member does not interfere with effective fluid communication between the various members comprising the core 42 of the present invention.

(2) Resilient Members

Resilient members may also be provided to the sanitary napkin of the present invention to improve resistance to distortion of the sanitary napkin, particularly as the sanitary napkin becomes wet with bodily fluids (i. e., improve bunching resistance). A method to measure resiliency for such resilient members can be found in copending U.S. patent application Ser. No. 08/241,430, filed in the name of Olsen, et al. on May 11, 1994, the disclosure of which is incorporated herein by reference. Typically, such members comprise a material that is resistant to bodily fluids so, even if the sanitary napkin becomes wet with such fluids, the resilient member can continue to provide bunching resistance. Exemplary resilient members are disclosed in U.S. Pat. No. 4,195,634, issued to DiSalvo on Apr. 1, 1980 and in U.S. Pat. No. 4,886,513, issued to Mason, Jr., et al. on Dec. 12, 1989. When a resilient member is provided to the sanitary napkin of the present invention it is positioned between the absorbent core 42 and the backsheet 40. Although many geometric shapes (oval, square, irregular, etc.) are suitable, such a resilient member is preferably rectangular in shape and has a longitudinal length substantially equal to the length of the central region 32 and a transverse width less than the width of the main body portion 21 at the transverse centerline T. Such a resilient member is preferably joined one or both of the absorbent core 42 and the backsheet 40 using means similar to those described above for joining the storage/distribution member 46 to underlying components.

As noted above resilient members are preferably resistant to bodily fluids such that they provide the requisite bunching resistance throughout the wear cycle of the sanitary napkin. Suitable materials include cross-linked cellulosic fibers, meltblown webs, thermoplastic polyethylene or polypropylene, synthetic foams, films or suitable blends of the types of materials described herein. Particularly preferred is the radiation cross-linked polyethylene foam known as VOLARA which is available from Voltek Corp., Lawrence, Mass.

(3) Other Suitable Sanitary Napkin Structures

While preferred sanitary napkin embodiments of the present invention have been described, numerous other sanitary napkin embodiments are disclosed in the literature. These could also be adapted to be provided with the clean appearance and the capacity signal means of the present invention. Several such sanitary napkins are disclosed in U.S. Pat. No. 4,425,130, issued to Desmarais on Jan. 10, 1984; U.S. Pat. No. 4,321,924, issued to Ahr on Mar. 30, 1982; the aforementioned U.S. Pat. No. 4,950,264 issued to Osborn on Aug. 21, 1990; U.S. Pat. No. 5,007,906 issued to Osborn, et al. on Apr. 16, 1991; the aforementioned U.S. Pat. No. 5,009,653 issued to Osborn on Apr. 23, 1991; U.S. Pat. No. 4,917,697 issued to Osborn et al. on Apr. 17, 1990, U.S. Pat. No. 5,171,302, issued to Buell on Dec. 15, 1992; U.S. Pat. No. 5,197,959, issued to Buell on Mar. 30, 1993; and in U.S. Pat. No. 5,324,278, issued in the name of Visscher, et at. on Jun. 28, 1994; U.S. patent application Ser. No. 07/630,451, filed in the name of Osborn et al. on Dec. 19, 1990 (PCT Publication No. 92 WO/10984, published Jul. 9, 1992); U.S. Pat. No. 5,346,486 issued to Osborn, et al.; and in U.S. patent application Ser. No. 07/874,872, filed in the name of Osborn on Apr. 28, 1992.

The sanitary napkin described herein can also be comprised one or more extensible components. In one preferred embodiment, most or all of the components are extensible to provide a degree of overall extensibility (on the order of 15%–40%) to the sanitary napkin. This extensibility may provide better in-use fit and comfort. In a particularly preferred alternative embodiment, the sanitary napkin is comprised of components that are extensible (preferably, capable of stretching), particularly in the longitudinal direction when the sanitary napkin is worn. Suitable extensible absorbent articles are described in U.S. patent application Ser. No. 07/915,133, filed in the name of Osborn, et al. on Jul. 23, 1992 (PCT Publication No. WO 93/01785 published Feb. 4, 1993).

In addition, other sanitary napkins that may be provided with the clean appearance and the capacity signal means of the present invention are described in the following pending U.S. patent applications which were filed on Jul. 23, 1992: U.S. patent application Ser. No. 07/915,202, filed in the name of Theresa L. Johnson, et al. (PCT Publication No. WO 93/01781); U.S. patent application Ser. No. 07/915,285, filed in the name of Thomas W. Osborn, et al. (PCT Publication No. WO 93/01782); U.S. patent application Ser. No. 07/915,201, filed in the name of Robb E. Olsen, et al. (PCT Publication No. WO 93/01783); and, U.S. patent application Ser. No. 07/915,134, filed in the name of Hines, et al. (PCT Publication No. WO 93/01784).

The terms "panty liner" or "pantiliner" refer to absorbent articles that are less bulky than sanitary napkins which are generally worn by women between their menstrual periods. The basic structure of an absorbent article in the form of a pantiliner which could be provided with the capacity signal means of the present invention is disclosed in U.S. Pat. No. 4,738,676, issued to Osborn on Apr. 19, 1988. For example, the resilient member described in the aforementioned U.S. Pat. No. 4,738,676 could be disposed only in the middle region of such a pantiliner and would preferably comprise the wet laid, tri-component members described above with respect to the storage/distribution member. Tissue, such as air laid or wet laid tissue, could be disposed between the bottom overwrap described in the aforementioned U.S. Pat. No. 4,738,676 and the modified resilient member described above such that it extended laterally into the side regions of the modified Osborn pantiliner. Such tissue, positioned as described, would be suitable for use as an indicator member for this alternative embodiment of the present invention. A particularly preferred tissue is the air laid tissue having a basis weight of about 35 gsm such as is available from Merlin Hygiene Products Ltd., Delta, BC, Canada.

The term "incontinence article" refers to pads, undergarments (pads held in place by a suspension system of same type, such as a belt, or the like), inserts for absorbent articles, capacity boosters for absorbent articles, briefs, bed pads, and the like, regardless of whether they are worn by adults or other incontinent persons. Suitable incontinence articles that can be provided with the clean appearance and the capacity signal means described herein are disclosed in U.S. Pat. No. 4,253,461 issued to Strickland, et al. on Mar. 3, 1981; U.S. Pat. Nos. 4,597,760 and 4,597,761 issued to Buell; U.S. Pat. No. 4,704,115; U.S. Pat. No. 4,909,802 issued to Ahr, et al.; U.S. Pat. No. 4,964,860 issued to Gipson, et al. on Oct. 23, 1990;U.S. Pat. No. 5,304,161 issued to Noel, et al. on Apr. 19, 1994; and U.S. Pat. No. 5,300,054 issued to Feist, et al. on Apr. 5, 1994.

3. Test Methods

Except as may be noted in a specific test method, all tests should be conducted at 73° F. and 50% relative humidity and all samples all samples should be conditioned at this temperature and humidity for at least two hours prior to testing.

A. Caliper

Caliper or thickness measurements for purposes of the present invention should be made when the sample is under a confining pressure of 0.1 psi (350 Pa).

A sample for caliper measurement is provided. A cylinder having a 1 in$^2$ (6.5 cm$^2$) circular surface area is punched out of the sample using a sharpened, circular die. A dial-type gauge suitable for making caliper measurements is positioned on the sample. Any gauge fitted with a foot having a circular surface area of at least 1 in$^2$ (6.5 cm$^2$) and capable of measuring caliper dimensions to 0.001 in (0.025 mm) can be employed. Examples of such gauges are an Ames model 482 (Ames Co.; Waltham, Mass.) or an Ono-Sokki model EG-225 (Ono-Sokki Co., Ltd.; Japan). Caliper measurements of three separate samples are taken. The reported caliper is the average of the measurements.

B. Density

Density (grams per cubic centimeter-g/cc) may be calculated from the basis weight (grams per square meter-gsm)

and the caliper (centimeters-cm) as measured under a given confining pressure, such as 0.10 psi, utilizing the formula:

Density$(g/cc)$=Basis weight$(gsm)$/[10,000×Caliper$(cm)$]

C. Vertical Wicking Height

1. Preparation of Artificial Menstrual Fluid

Artificial Menstrual Fluid (AMF) is prepared by combining equal volumes of gastric mucin solution and fresh, sterile defibrinated sheep blood (Cleveland Scientific, American Biomedical, Bath, Ohio). The gastric mucin solution is prepared by combining the following in the proportions and order shown:

450 ml of aqueous sodium dihydrogen phosphate (0.138 wt. %) solution containing sodium chloride (0.85 wt. %) adjusted to pH 7.2±0.1;

7.5 ml potassium hydroxide aqueous solution;

31 g sterilized gastric mucin (ICN Biomedical Inc., Cleveland, Ohio); heated 2.5 hours to completely dissolve the gastric mucin. The solution is allowed to cool to less than 40° C.;

2.0 ml of 8 wt. % aqueous lactic acid solution.

The mixture is autoclaved at 121° C. for 15 minutes, then allowed to cool to room temperature. This mixture should be refrigerated and should be used within 7 days.

2. Sample Preparation

Samples are cut into 2.54 cm width strips about 25 cm long. Two samples are cut for each material to be tested. The samples are sealed in plastic on the top and on both long sides using a T-Bar sealer (Model T-7, 115VAC, 65 W Harwil Company, Santa Monica, Calif.) allowing 0.5 cm to remain uncovered at the bottom. The 0.5 centimeter at the bottom of the material strip remains exposed. The outside of the plastic is graduated with marks each centimeter along the length of the sample, starting at the bottom of the plastic (not the bottom of the sample).

3. Equipment Preparation

The AMF is stirred for 30 minutes at 22° C. Approximately 300 ml of the equilibrated AMF is poured into a 500 ml recrystallizing dish. The filled dish is stirred magnetically at low speed.

A cylindrical Plexiglas bar (30.5 cm cylindrical bar with at least two attached Plexiglas plates (25 cm×0.5 cm×3 cm) attached at the end with the spacing being adjustable) is clamped onto a ring stand. The clamp should tentatively be set approximately 18–20 inches above the base of the stand with the long dimension of the Plexiglas plates being oriented vertically. Allow enough space between the Plexiglas plates on the end of the cylindrical bar to allow the samples to be tested to be placed between them.

4. Test Procedure

The sealed top side of the sample is placed between two of the Plexiglas plates, and then the plates are tightened together until the sample is completely suspended. There should be enough room along the width of the plates to fit 2–3 samples without the samples touching. If not, additional plates can be used to position the samples one behind the other. After suspending all samples, the bottom and top of the samples should all be level with respect to the Plexiglas plates and each other.

The stir plate and dish of AMF is placed directly underneath the suspended samples. The samples are lowered such that 0.5 cm of each sample is submerged in the AMF. (The plastic covered portion of the samples should not be submerged., as fluid will tend to wick in the interfaces of the seal instead of within the sample). Adjustments to level the bar and samples are made, if necessary, so that each sample bottom is equally submerged in the AMF.

The samples are suspended in the stirred AMF to the bottom of the plastic. The fluid height reached after the fluid front (leading edge thereof) has reached an equilibrium height (about 12 hours equilibration time) is recorded. The average height of the fluid front in these samples is approximated. Heterogeneity within a sample may provide channels of wicked fluid with no clear leading edge. If so, the midpoint of the wicked height is taken as the value to be recorded. The average of the final vertical wicking values recorded for the samples (n=2) is used as the vertical wicking value for the material.

The disclosures of all patents, patent applications (and any patents which issue thereon, as well as any corresponding published foreign patent applications), and publications mentioned throughout this patent application are hereby incorporated by reference herein. It is expressly not admitted, however, that any of the documents incorporated by reference herein teach or disclose the present invention. It is also expressly not admitted that any of the commercially available materials or products described herein teach or disclose the present invention.

While particular embodiments of the present invention have been illustrated and described, it would be obvious to those skilled in the art that various other changes and modifications can be made without departing from the spirit and scope of the invention.

What is claimed is:

1. A sanitary napkin for absorbing bodily fluids having a longitudinal centerline, a transverse centerline, and a main body portion having longitudinally oriented sides, transversely oriented ends, a pair of longitudinally oriented side regions, and a longitudinally oriented middle region therebetween, said sanitary napkin comprising:

a liquid permeable topsheet;

a liquid impermeable backsheet; and an absorbent core disposed between said topsheet and said backsheet, said absorbent core comprising:

an acquisition member in effective fluid communication with said topsheet and disposed beneath said topsheet in said middle region, wherein said acquisition layer has sufficient hiding power so that said acquisition member at least partially minimizes the visual impact of absorbed bodily fluids, a storage/distribution member having an absorbent capacity, said storage/distribution member contacting said acquisition member, being in effective fluid communication with said acquisition member, and being disposed beneath said acquisition member along said longitudinal centerline defining said middle region, and an indicator member in effective fluid communication with said storage/distribution member, at least a portion of said indicator member being disposed between said topsheet and said backsheet in at least one of said side regions, wherein the ratio of the vertical wicking height of said storage/distribution member to the vertical wicking height of said acquisition member is equal to or greater than about 1.5:1.

2. A sanitary napkin according to claim 1 wherein the ratio of the vertical wicking height of said storage/distribution member to the vertical wicking height of said indicator member is equal to or greater than about 1.5:1.

3. A sanitary napkin according to claim 1 wherein the ratio of the vertical wicking height of said storage/distribution member to the vertical wicking height of either of said acquisition member or said indicator member is equal to or greater than about 2.0:1.

4. A sanitary napkin according to claim 1 wherein said main body portion further comprises first and second end regions adjacent said transversely oriented ends and a central region therebetween and said sanitary napkin further comprises a pair of flaps joined to said main body portion in said central region wherein one of said flaps extends laterally outwardly from each of said sides.

5. A sanitary napkin according to claim 4 wherein said flaps comprise extensions of other components of said sanitary napkin.

6. A sanitary napkin according to claim 5 wherein said flaps comprise extensions of said topsheet and said backsheet.

7. A sanitary napkin according to claim 4 wherein said flaps comprise a separate element joined to said main body portion.

8. A sanitary napkin according to claim 1 wherein said storage/distribution member comprises a wet laid tri-component member.

9. A sanitary napkin according to claim 8 wherein said wet laid tri-component member comprises between about 20% and about 80% chemically stiffened, twisted, and cured fibers, between about 10% and about 80% eucalyptus high surface area fiber, and between 0% and about 50% thermoplastic binding means.

10. A sanitary napkin according to claim 9 wherein said wet laid tri-component member comprises between about 45% and about 60% chemically stiffened, twisted, and curled fibers, between about 30% and about 45% eucalyptus high surface area fiber, and between 5% and about 15% thermoplastic fibrous binding means.

11. A sanitary napkin according to claim 10 wherein said wet laid tri-component member comprises about 60% chemically stiffened, twisted, and curled fibers, about 30% eucalyptus high surface area fiber, and about 10% thermoplastic fibrous binding means.

12. A sanitary napkin according to claim 10 wherein said wet laid tri-component member further comprises end portions lying in said end regions of said main body portion, wherein said end portions comprise a mixture of a fibrous material and a material which contains fluids by osmotic means.

13. A sanitary napkin according to claim 1 wherein said acquisition member and said indicator member comprise an air laid fibrous assembly.

14. A sanitary napkin according to claim 13 wherein the caliper of said acquisition member is between about 12 mm and 17 mm.

15. A sanitary napkin for absorbing bodily fluids having a longitudinal centerline, a transverse centerline, and a garment surface, said sanitary napkin comprising:

a main body portion having longitudinally oriented sides, transversely oriented ends, a pair of longitudinally oriented side regions, a longitudinally oriented middle region therebetween, first and second end regions adjacent said transversely oriented ends, and a central region therebetween, said main body portion comprising:

a liquid permeable topsheet;

a liquid impermeable backsheet;

an absorbent core disposed between said topsheet and said backsheet, said absorbent core comprising:

a pair of indicator members, one of said indicator members being disposed between said topsheet and said backsheet adjacent each of said sides and defining said side regions, said indicator members comprising an air laid fibrous assembly, a storage/distribution member having an absorbent capacity and disposed on said backsheet in said middle region, said storage/distribution member comprising a wet laid tri-component member, and an acquisition member disposed between said storage/distribution member and said topsheet, said acquisition member being in contact with said storage/distribution member and comprising an air laid fibrous assembly, wherein said acquisition member has sufficient hiding power so that said acquisition member at least partially minimizes the visual impact of absorbed bodily fluids, wherein the ratio of the vertical wicking height of said storage/distribution member to the vertical wicking height of said acquisition member is equal to or greater than about 1.5:1; and a pair of flaps joined to said main body portion in said central region wherein one of said flaps extends laterally outwardly from each of said sides.

16. A sanitary napkin according to claim 15 further comprising attachment means disposed on said garment surface of said main body portion of said sanitary napkin and on said garment surface of said flaps of said sanitary napkin.

17. A sanitary napkin according to claim 16 wherein said topsheet comprises an apertured formed film.

18. A sanitary napkin according to claim 17 wherein the caliper of said acquisition member is between about 12 mm and 17 mm.

19. A sanitary napkin for absorbing bodily fluids having a longitudinal centerline, a transverse centerline, and a garment surface, said sanitary napkin comprising:

a main body portion having longitudinally oriented sides, transversely oriented ends, a pair of longitudinally oriented side regions, and a longitudinally oriented middle region therebetween, said main body portion comprising:

a liquid permeable topsheet;

a liquid impermeable backsheet;

an absorbent core disposed between said topsheet and said backsheet, said absorbent core comprising:

a pair of indicator members, one of said indicator members being disposed between said topsheet and said backsheet adjacent each of said sides and defining said side regions, said indicator members comprising an air laid fibrous assembly, an acquisition member disposed between said topsheet and said backsheet in said middle region, and a storage/distribution member which: contacts said acquisition member, is disposed in said middle region, and underlies said acquisition member, wherein the ratio of the vertical wicking height of said storage/distribution member to the vertical wicking height of said acquisition member is equal to or greater than about 1.5:1;

wherein said topsheet is also disposed between said acquisition member and said indicator member.

20. A sanitary napkin according to claim 19 wherein said acquisition member at least partially minimizes the visual impact of absorbed bodily fluids.

* * * * *

UNITED STATES PATENT AND TRADEMARK OFFICE
CERTIFICATE OF CORRECTION

PATENT NO. : 5,647,863  
DATED : July 15, 1997  
INVENTOR(S) : John L. Hammons

Page 1 of 1

It is certified that error appears in the above-identified patent and that said Letters Patent is hereby corrected as shown below:

Column 4,
Line 33, "comers" should read -- corners --.

Column 16,
Line 10, "MeNair" should read -- McNair --.

Column 23,
Line 22, "cured" should read -- curled --.

Signed and Sealed this

Eighth Day of January, 2002

*Attest:*

*Attesting Officer*

JAMES E. ROGAN  
*Director of the United States Patent and Trademark Office*